United States Patent [19]
Ruiz et al.

[11] Patent Number: 5,912,149
[45] Date of Patent: Jun. 15, 1999

[54] MULTIMERIC SELF-CLEAVING RIBOZYME

[75] Inventors: Juan Ruiz, Pamplona, Spain; George Y. Wu, Avon, Conn.

[73] Assignee: The University of Connecticut, Farmington, Conn.

[21] Appl. No.: 08/719,353

[22] Filed: Sep. 25, 1996

Related U.S. Application Data

[60] Provisional application No. 60/004,316, Sep. 26, 1995.
[51] Int. Cl.$^6$ .......................... C07H 21/02; C07H 21/04; C12N 5/10; C12N 15/11
[52] U.S. Cl. ..................................... 435/91.31; 435/320.1; 435/325; 435/375; 536/23.1; 536/24.5; 536/25.1
[58] Field of Search ........................... 435/6, 91.3, 91.31, 435/91.33, 172.3, 238, 320.1, 325, 375; 514/44; 536/23.1, 25.1, 24.5; 935/33, 34, 36

[56] References Cited

U.S. PATENT DOCUMENTS 5,500,357   3/1996   Taira et al. ............................ 435/91.31

FOREIGN PATENT DOCUMENTS

WO91/11511   8/1991   WIPO .

OTHER PUBLICATIONS

Chen et al., "Multitarget–ribozyme directed to cleave at up to nine highly conserved HIV–1 env RNA regions inhibits HIV–1 replication–potential effectiveness against most presently sequenced HIV–1 isolates", *Nucleic Acids Research* 20 (17):4581–4589 (1992).

Ohkawa et al., "Importanace of independence in ribozyme reactions: Kinetic behavior of trimmed and of simply connected multiple ribozymes with potential activity against human immunodeficiency virus", *PNAS USA* 90:11302–11306 (1993).

Weizsäacker et al., "Cleavage of hepatitis B virus RNA by three ribozymes transcribed from a single DNA template", *Biochem. Biophys. Res. Commun.* 189(2):743–748 (1992).

Chowrira et al., "*In Vitro* and *in Vivo* Comparison of Hammerhead, Hairpin, and Hepatitis Delta Virus Self–processing Ribozyme Cassettes", *J. Biol. Chem.* 269(41):25856–25864 (1994).

He et al., "In vitro cleavage of HPV16 E6 and E7 RNA fragments by synthetic ribozymes and transcribed ribozymes from RNA–trimming plasmids", *FEBS Lett.* 322(1):21–24 (1993).

Taira et al., "Construction of a novel RNA–transcript–trimming plasmid which can be used both in vitro in place of run–off and (G)—free transcriptions and in vivo as multi-sequences transcription vectors", *Nucleic Acids Research* 19(19):5125–5130.

Yuyama et al., "Construction of a tRNA–embedded–ribozyme trimming plasmid", Biochem. Biophys. Res. Commun. 186 (3):1271–1279 (1992).

(List continued on next page.)

*Primary Examiner*—George C. Elliott
*Assistant Examiner*—Thomas G. Larson
*Attorney, Agent, or Firm*—Hamilton, Brook, Smith & Reynolds, P.C.

[57]   ABSTRACT

The invention pertains to a multimeric self-cleaving ribozyme comprising multiple repeating units, wherein each unit comprises a ribozyme containing a catalytic domain and an antisense domain, and a target recognition sequence or portion thereof recognized by the antisense domain of the ribozyme and comprising a ribozyme cleavage site to facilitate self-cleavage. The invention also pertains to constructs comprising DNA encoding the multimeric self-cleaving ribozyme, cells stably transformed with these constructs, and methods of cleaving RNA, regulating gene expression and generating molecular weight ladders utilizing the multimeric self-cleaving ribozyme.

14 Claims, 7 Drawing Sheets

OTHER PUBLICATIONS

Yuyama et al., "A multifunctional expression vector for an anti–HIV–1 ribozyme that produces a 5'—and 3'—trimmed trans–acting ribozyme, targeted against HIV–1 RNA, and cis–acting ribozymes that are designed to bind to and thereby sequester trans–activator proteins such as Tat and Rev", *Nucleic Acids Research* 22 (23):5060–5067 (1994).

Haseloff and Gerlach, "Simple RNA enzymes with new and highly specific endoribonuclease activities", *Nature* 334(18):585–591 (1988).

Bratty et al., "The hammerhead RNA domain, a model ribozyme", *Biochimica et Biophysica Acta* 1216:345–359 (1993).

Ventura et al., "Activation of HIV–specific ribozyme activity by self–cleavage", *Nucleic Acids Research* 21(14):3249–3255 (1993).

Paillard et al., "Nuclear Antisense Gene Therapy for HIV–1", (conference Abstract) *Gene Ther. Meet., Cold Spring Harbor* 133: (1994).

Nürnberg, "DIG–Labeled RNA In Situ Hybridization Without Coverslipping", *Biotechniques* 18(3):406–408 (1995).

Borneman and Altshuler "Simple Method to Produce RNA Size Markers Using cis Ribozymes", *Biotechniques* 18(3):404–406 (1995).

Breaker and Joyce, "Inventing and Improving Ribozyme Function: Rational Design Versus Iterative Selection Methods", *Trends Biotechnol*, 12:268–275 (1994).

Altman S., "RNA Enzyme–Directed Gene Therapy", *Proc. Natl. Acad. Sci. U.S.A.*, 90:10898–10900 (1993).

Long and Uhlenbeck, "Self–cleaving catalytic RNA", *FASEB Journal* 7:25–30 (1993).

BASIC UNIT IN TWO POSSIBLE DIRECTIONS

Xba1→Spe1     Spe1←Xba1

LIGATION WITH T4 DNA LIGASE (PRODUCTION OF A TANDEM OF N COPIES WITH N=8)

1　　　　　2　　　　　3　　　　　4　　　　　5　　　　　6　　　　　7　　　　　8
Spe1←Xba1 Spe1←Xba1 Xba1→Spe1 Spe1←Xba1 Xba1→Spe1 Xba1→Spe1 Xba1→Spe1 Xba1→Spe1

DIGESTION WITH Xba1 AND Spe1 no　　　　Xba1　　　Spe1　　　　　　　　Xba1　　　　　　　　no　　　　　no
　cleavage　cleavage　cleavage　　　　　cleavage　　　　　cleavage　cleavage
　　 ↓　　　　 ↓　　　　 ↓　　　　　　　　 ↓　　　　　　　　 ↓　　　　　 ↓
1　　　　　2　　　　　3　　　　　4　　　　　5　　　　　6　　　　　7　　　　　8
Spe1←Xba1 Spe1←Xba1 Xba1→Spe1 Spe1←Xba1 Xba1→Spe1 Xba1→Spe1 Xba1→Spe1 Xba1→Spe1

DIGESTION PRODUCTS (SEPARATION THROUGH AGAROSE GEL ELECTROPHORESIS)

1　　　　　2　　　　　3　　　　　4
Spe1←Xba1 Spe1←Xba1 Xba1→Spe1 Spe1←Xba1

5　　　　　6　　　　　7　　　　　8
　　　　　　　　　Xba1→Spe1 Xba1→Spe1 Xba1→Spe1 Xba1→Spe1

LINEARIZATION OF PLASMID WITH Xba1 AND/OR Spe1 and LIGATION

FIG. 7

MULTIMERIC SELF-CLEAVING RIBOZYME

RELATED APPLICATIONS

The present application claims priority to U.S. provisional application Ser. No. 60/004,316, filed Sep. 26, 1995, the teachings of which are incorporated herein by reference in their entirety.

GOVERNMENT SUPPORT

Work described herein was supported by grant NIH DK-42182 from the National Institutes of Health. The U.S. government has certain rights in the invention. Work described herein was also supported by Fundacion Ramon Areces, Spain.

BACKGROUND OF THE INVENTION

Ribozymes are catalytic RNA molecules with endoribonuclease activity. The molecule can be divided into two different domains: the antisense portion, responsible for the recognition of and binding to the target RNA, and the catalytic domain which causes cleavage of the RNA. Modification of the antisense domain allows the redirection of the specificity of the molecule without affecting its catalytic properties. This makes it possible to down-regulate the amount of any given messenger RNA inside a cell, as long as the target sequence is known and contains potential ribozyme sites.

Ribozymes can be useful in solving a variety of problems, including viral disease infection and the process of malignant transformation. Although ribozymes are technically similar to antisense oligodeoxynucleotides (ODN) and antisense RNAs (AR), they have the advantage of catalytic activity that potentially allows a single molecule to destroy more than one target RNA. Despite this catalytic activity, a large molar excess of ribozyme over substrate is usually needed to get a significant reduction in the level of messenger RNA. Although this difficulty is possibly related to the intracellular localization of target RNA and ribozymes, another problem results from secondary structures formed by the target RNA and ribozyme which interfere with the necessary hybridization between the two structures.

In vitro cleavage studies utilize substrate and ribozyme transcripts which are usually shorter than their cellular counterparts. Specifically, expression vectors responsible for the synthesis of the ribozyme inside the cell contribute sequences upstream and downstream from the ribozyme motif to the final molecule, sequences which are not present in ribozymes synthesized in vitro. Nonproductive folding and non-specific hybridization of the ribozyme due to these extra sequences likely accounts for a portion of the loss of activity observed in vivo.

One possible solution to this problem is the use of chemically synthesized ribozymes. These molecules have the advantage of lacking the extra sequences, and they can be modified to make them more resistant to RNAses. However, when prolonged activity is needed, such chemically synthesized molecules require repeated administrations. Another possibility is to improve the activity of the ribozymes synthesized inside the cells by multiplying the number of catalytic molecules per cell or by increasing the activity of the individual molecules. Prior work has connected several ribozyme molecules within an expression vector (Chen et al., *Nucleic Acids Research* 20:4581–4589 (1992); Ohkawa et al,. *PNAS USA* 90:11302–11306 (1993); Weizsacker et al., *Biochem. Biophys. Res. Commun.* 189:743–748 (1992)). One problem with these systems is that, after a certain number, the addition of more units to the construct does not correlate with an increase in the activity of the molecule, probably as a result of non-productive folding of the molecules which does not allow all of the units to interact with the target.

Others have used cis-acting ribozymes to reduce to a minimum the extra sequences upstream and/or downstream of the trans-acting motif (Chowrira et al., *J. Biol. Chem.* 269:25856–25864 (1994); He et al., *FEBS Lett.* 32:21–24 (1993); Taira et al., *Nucleic Acids Research* 19:5215–5130 (1991); Yuyama et al., *Biochem. Biophys. Res. Commun.* 186:1271–1279 (1992); Yuyama et al., *Nucleic Acids Research* 23:5060–5067 (1994)). Shotgun-type ribozyme expression vectors have also been designed in which tandems of transacting ribozymes are released by other (different) cis-acting ribozymes within the vector (Ohkawa et al., (1993)). However, the number of ribozyme monomers which can be incorporated in a single transcript is limited in this approach.

SUMMARY OF THE INVENTION

This invention pertains to a novel multimeric ribozyme comprising multiple repeats of a self-cleavable molecule capable of functioning as a cis and trans ribozyme concurrently. This invention has the advantage of exploiting the versatility of expression vectors to synthesize the ribozyme inside the cell without the impairment of ribozyme activity often caused by vector-contributed sequences upstream and downstream from the ribozyme motif. This invention also has the advantage of delivering high numbers of ribozyme monomers comparable in size to those produced by chemical synthesis. The self-cleavage kinetics and trans cleavage activity of this multimeric ribozyme with respect to the target RNA transcript are described herein, along with techniques for the cloning of vectors containing multiple copies of the monomeric ribozyme unit.

The multimeric self-cleaving ribozyme comprises multiple repeating units, wherein each unit comprises a ribozyme (preferably a hammerhead ribozyme) and an oligonucleotide sequence comprising the target recognition sequence or a portion thereof which contains a ribozyme cleavage site and is recognized by the antisense region of the ribozyme.

Simultaneous with transcription of the ribozyme, the antisense region of the molecule recognizes and binds to the target recognition sequence or portion thereof within the ribozyme transcript, thus inducing the cis catalytic activity of the molecule and resulting in cleavage of the ribozyme transcript at the target recognition site. The cleaved unit, or monomeric, ribozyme is thus liberated from the rest of the transcript and can then act in trans to recognize, bind and cleave the target RNA transcript, which transcript contains the target recognition sequence, comprising a ribozyme cleavage site, recognized by the antisense region of the ribozyme.

In one embodiment of the invention, the ribozyme recognizes, binds and cleaves a target RNA transcript from the core region of the pregenomic hepatitis B virus (HBV) RNA, which transcript contains a target recognition sequence that is recognizable by the ribozyme. In a further embodiment of the invention, the HBV RNA target recognition sequence is nucleotides 2021 to 2045 (AAGCCUUAGAGUCUCCUGAGCAUUG, SEQ ID NO.: 1) of HBV, with cleavage occurring at nucleotide 2033.

The present invention also relates to constructs and vectors comprising DNA sequences encoding the multimeric ribozyme of the present invention. The present invention further relates to cells stably transformed with the vectors and constructs of the present invention.

The present invention also pertains to methods of regulating gene expression. Specifically, the expression of a gene or portion thereof can be down-regulated according to the present invention by cleavage of RNA which has been transcribed from the gene or portion thereof. The multimeric ribozyme described herein acts in trans to efficiently cleave the target RNA transcript at the ribozyme cleavage site located within the target recognition sequence, resulting in RNA fragments which are quickly degraded in the cell.

Thus, this invention has application to several areas. The multimeric self-cleavable ribozymes of the present invention have utility for RNA-targeted gene therapy to down-regulate endogenous gene expression by cleaving mRNA transcripts produced by a gene of interest. For instance, the multimeric self-cleaving ribozyme of the present invention can be used to target and cleave RNA in order to inhibit the replication cycle of viruses such as HIV, hepatitis B virus (HBV), bovine leukemia virus (BLV) and human T-cell leukemia viruses (HTLV-I and -II).

The multimeric self-cleavable ribozyme of the present invention can also be used to inhibit expression of genes belonging to other infectious agents, including viruses, bacteria and protozoa, or genes whose products have deleterious effects on an organism in particular situations (i.e., inflammation in autoimmune diseases, vascular restenosis after angioplasty, defective metabolic enzymes such as the alpha-1-antitrypsin). The present invention also has application to genes involved in the control of cell growth and differentiation, such as oncogenes. The ribozyme of the present invention can also be used in virtually any application in which highly efficient, sequence-specific cleavage and destruction of RNA transcripts is desired.

These multimeric self-cleavable molecules also have practical application as RNA molecular weight markers or in preparing an RNA molecular weight ladder. Multiple fragments of predictable size can be generated and used as standards to determine molecular weights of unknown RNAs. Present technology utilizes different templates for the synthesis of the bands in commercially available RNA molecular weight markers. The present system requires only one template, considerably reducing the amount of necessary time and work.

BRIEF DESCRIPTION OF THE DRAWINGS

FIG. 1A shows the sequences of the two oligonucleotides (SEQ ID NO: 3 (top) and SEQ ID NO: 4 (bottom)) used for the cloning of the basic unit of the multimeric ribozyme, including the restriction enzyme sites for the isoschizomer enzymes (XbaI and SpeI) as well as for HindIII, used for the cloning of pBMRz and BamHI, used for the cloning of pBRz. FIG. 1B depicts the structure of the trans-acting ribozyme (left) (SEQ ID NO: 2) and the self-cleaving ribozyme (right) (SEQ ID NO: 6). The recognition sequences are represented as the 24 nucleotide HBV RNA target (top line in trans-acting ribozyme) (SEQ ID NO: 1) and the 11 nucleotide (SEQ ID NO: 5) self-recognition sequence (hybridizing through a loop at the 3' end of the ribozyme) present downstream of the catalytic domain in the cis-acting ribozyme.

FIG. 2A shows the single ribozymes BamHI and PvuII; thin lines represent plasmid-derived sequences and thick lines represent the ribozyme motif. FIG. 2B shows the in vitro transcript of the 5-copy ribozyme construct (pB5T-MRz), as well as its relationship with the basic cloning unit and the monomer released by self-cleavage.

DETAILED DESCRIPTION OF THE INVENTION

The simplicity of the design and the specificity of the enzymatic activity of ribozymes make them potentially valuable tools for both research and clinical applications. However, several difficulties presently prevent the widespread use of ribozyme technology. These difficulties are associated with three different types of problems: the difficulty in achieving co-localization of the ribozyme and target in the same subcellular compartment, the ability of the ribozyme to hybridize with its complementary region in the target RNA and the lack of turnover of the ribozyme once the cleavage reaction has been accomplished. The ultimate consequence of these problems is the need for great amounts of ribozyme molecules inside the cells to obtain a significant biologic effect.

The present invention pertains to a multimeric ribozyme comprising multiple repeats of a self-cleavable molecule able to act as a cis and trans ribozyme concurrently. The basic unit contains the sequence of a ribozyme, preferably a hammerhead ribozyme, active in cis against the multimeric ribozyme transcript and in trans against the target RNA transcript. In order to make the molecule self-cleavable, a target motif recognized by the antisense domain of the ribozyme (the target recognition sequence) was included in each monomeric unit. This target recognition sequence can be the complete sequence recognized by the ribozyme in the target RNA transcript, or it can be a portion of the full sequence which retains the ribozyme cleavage site and the capacity for recognition by the ribozyme.

The described design allows the ribozyme to act in cis, cleaving the transcript and liberating itself from sequences located 3' thereto. Using a novel method utilizing restriction enzymes which are isoschizomers, as described below, each monomeric ribozyme unit is operably linked to the following monomeric ribozyme unit. Thus, each ribozyme is in fact surrounded by the target recognition sequence; that is, the target recognition sequence which is downstream of the catalytic domain of one ribozyme monomer is upstream of the catalytic region of another ribozyme monomer. The cleavage reaction produces single ribozyme molecules which are liberated with minimum additional or vector-contributed sequences at the 5' and 3' ends.

Terms used herein have their art-recognized meaning unless otherwise indicated. As used herein, "cis", "in cis" and "cis activity" are defined to mean activity, particularly recognition, binding or cleavage activity, which is directed to the ribozyme transcript or ribozyme molecule itself. "Trans", "in trans" and "trans activity" are defined to mean activity, particularly recognition, binding or cleavage activity, which is directed to the target or non-ribozyme transcript or molecule. Also, as used herein, a "multimeric" ribozyme is defined to mean a ribozyme comprised of many linked monomeric units. The multimeric structure can comprise as few as two linked monomers; however, in a preferred embodiment, the multimeric ribozyme comprises from at least about five to at least about ten linked monomers. Generally, an increase in the number of monomers included in the multimeric ribozyme corresponds to an increase in the trans activity of the ribozyme since a greater number of ribozyme monomers will be released after cis cleavage of the multimeric ribozyme transcript.

Each monomer within the multimeric transcript comprises two portions: the ribozyme portion containing an antisense domain and a catalytic domain, and a second portion comprising the target recognition sequence which contains a ribozyme cleavage site and is recognizable by the antisense domain of the ribozyme.

The ribozyme portion can be a hammerhead ribozyme, a hairpin ribozyme, a delta virus motif ribozyme or neurospora ribozyme. Due to the shortness of the molecule, which allows easy in vitro synthesis and manipulation, the ribozyme will generally be a hammerhead ribozyme as described and constructed in Haseloff and Gerlach (*Nature* 334(18):585–591 (1988)) and Bratty et al. (*Biochimica et Biophysica Acta* 1216:345–359 (1993)), the teachings of which are incorporated herein by reference in their entirety.

The ribozyme comprises two main parts: the antisense domain, responsible for recognition of and binding to the target recognition site, and the catalytic domain, responsible for cleaving the bound RNA.

In the ribozyme of the present invention, the antisense domain can be tailored to recognize and bind particular, specific RNA target recognition sequences. For example, in one embodiment of the present invention, the antisense sequence of the ribozyme is CAAUGCUCAGGAACUC-UAAGGCUU (SEQ ID NO.: 2), which allows the ribozyme monomer to recognize and bind a specific sequence (AAGCCUUAGAGUCUCCUGAGCAUUG, SEQ ID NO.: 1) within the core region of the pregenomic RNA transcript of HBV. Alternatively, the antisense sequence can be altered to complement any known sequence, such that the ribozyme recognizes and binds almost any target recognition sequence.

The target recognition sequences which can be recognized by the ribozyme are many and varied. Hammerhead ribozymes can be designed to recognize and cleave virtually any RNA with some basic requirements. The recognition sequence around the cleavage point must be the triplet NUX, where N is any nucleotide and X represents A, U or C (Bratty et al., 1993). The most common triplet at the cleavage point is GUC (the only triplet sequence present in the virusoids where the hammerhead motif was described), although the triplet CUC and other variations also produce similar activity. As used herein, "ribozyme cleavage site" is defined to mean this required triplet recognition sequence surrounding the cleavage point.

The target recognition sequence incorporated in the multimeric ribozyme transcript to allow self-cleavage can be either the entire sequence which the ribozyme recognizes in the target RNA transcript or can be a portion thereof which contains a ribozyme cleavage site and which is recognized by the ribozyme. The target recognition sequence is located within each monomeric unit and can be either upstream or downstream of the ribozyme. As the ribozyme is transcribed, the antisense domain recognizes and binds the target recognition sequence and cleaves the transcript at the ribozyme cleavage site. Thus, the monomeric ribozyme unit is liberated from any excess 5' or 3' ends contributed by the vector, allowing the ribozyme to hybridize more specifically to the RNA target transcript at the target recognition sequence.

The simplicity of the cloning design allows the construction of multimeric ribozymes containing a number of monomers limited only by the insert size in the expression vector; generally, inserts of 5 to 7 kilobases, the equivalent to 70 to 100 connected ribozymes, can be inserted in adenoviral or retroviral vectors. The monomers released from such constructs will have the structure described herein.

Figure 4:
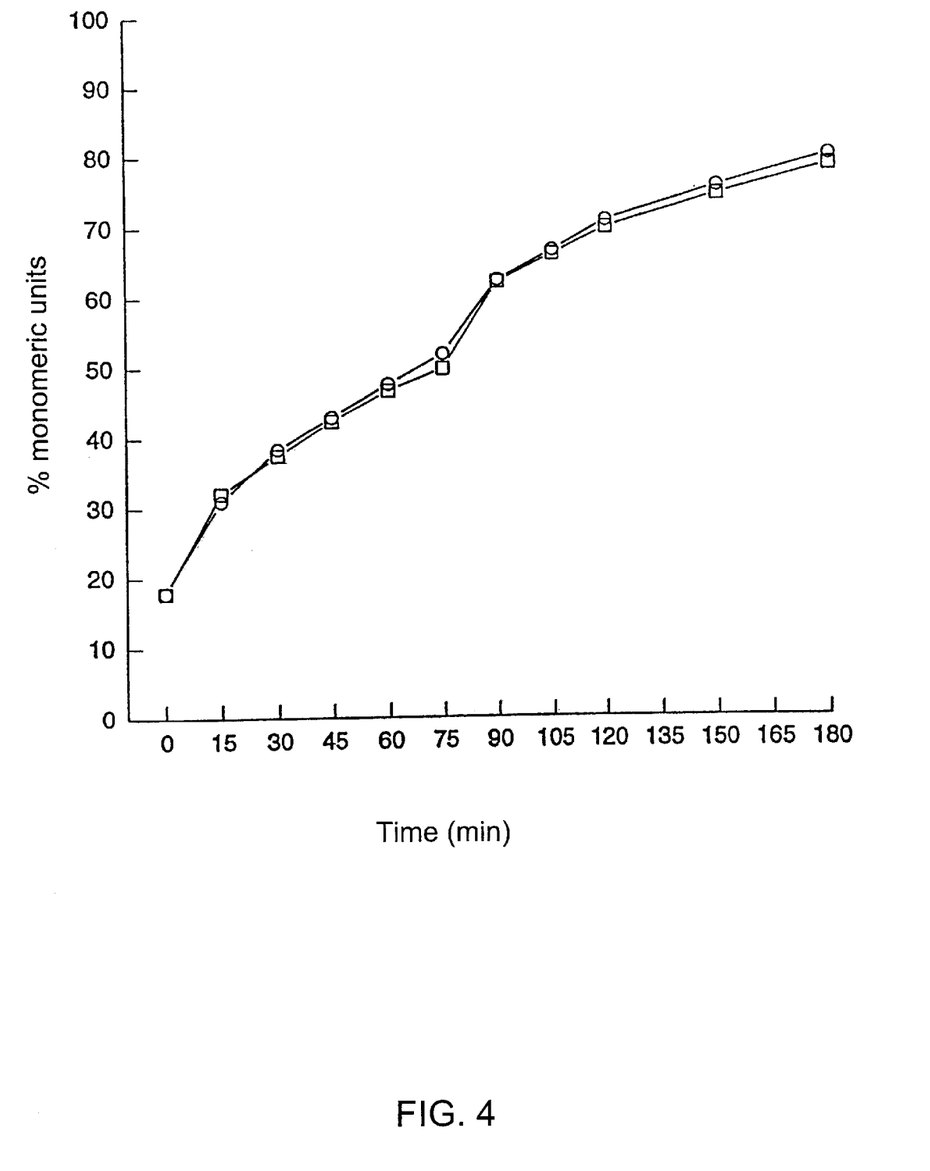
FIG. 4 is a graphic representation of the self-cleavage time course of a pentameric ribozyme and the influence of the target HBV RNA on the self-cleavage reaction. Incubation without target HBV RNA is indicated with an open circle. Incubation in the presence of target HBV RNA is indicated with an open square.

The results described herein confirm the feasibility of the above-described approach: multimeric ribozymes containing 5 and 10 copies of the monomeric ribozyme unit self-cleave, releasing monomers of the expected size. There are two important aspects related to this approach which make it extremely useful. The first is the fact that the self-cleavage of the transcripts seems to occur almost simultaneously with the transcription reaction, as indicated by the presence of extensive cleavage of the transcripts immediately following the RNA synthesis. The second is that the self-cleaving process is independent of the presence of the HBV target RNA (FIG. 4). This phenomenon is probably related to the folding of the multimeric transcript that favors the chances of self-hybridization.

A similar observation has been reported by others, showing the in vivo cleavage of a cis-ribozyme while the trans-acting counterpart, sharing the same target motif, was not active (Ventura et al. *Nucleic Acids Research* 21:3249–3255 (1993)). The fact that the self-cleavage motif is only 11 nucleotides long compared with the 24 nucleotides present in the target RNA does not decrease hybridization or catalytic cleavage and is not an impediment to the cis-reaction. On the contrary, the short self-cleaving motif assures that after the cleavage is complete, the small complementary ends will not interfere with the trans-hybridizing reaction.

Figure 1A:
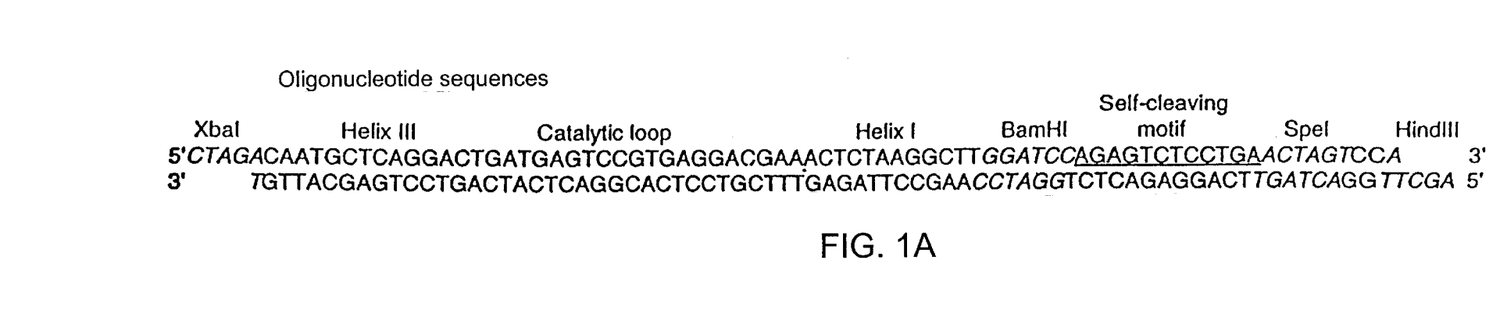
FIGS. 1A and 1B illustrate the basic ribozyme unit with the sequence of a hammerhead ribozyme active in trans against the pre-genomic RNA of the hepatitis B virus.

To compare the cleavage activities of monomers released from the multimeric ribozymes with that of regular single transcripts, two different single ribozymes were used (BamHI ribozyme and PvuII ribozyme, FIG. 1A). The ribozymes differed only in the length of the 3' tail of the molecule: the short ribozyme lacked any extra sequences following the catalytic molecule, whereas the long transcript contained 190 non-specific nucleotides derived from the transcription vector. As previously reported by other groups (Chowrira et al., (1994)), cleavage percentages with the long transcript are significantly smaller.

Comparison of the activity of these single ribozymes with the pentameric construct (pB5T-MRz) shows that the latter is more effective at cleaving the HBV RNA not only when equal numbers of transcripts have been used (ratios of 1:1 and 10:1 for both types of ribozymes) but also when the amount of pentameric molecules was 5 times less to compensate for the possible release of 5 monomers per transcript (ratios of 0.2:1 and 2:1 for pentameric ribozymes against 1:1 and 10:1 for single ribozymes).

Figure 6:
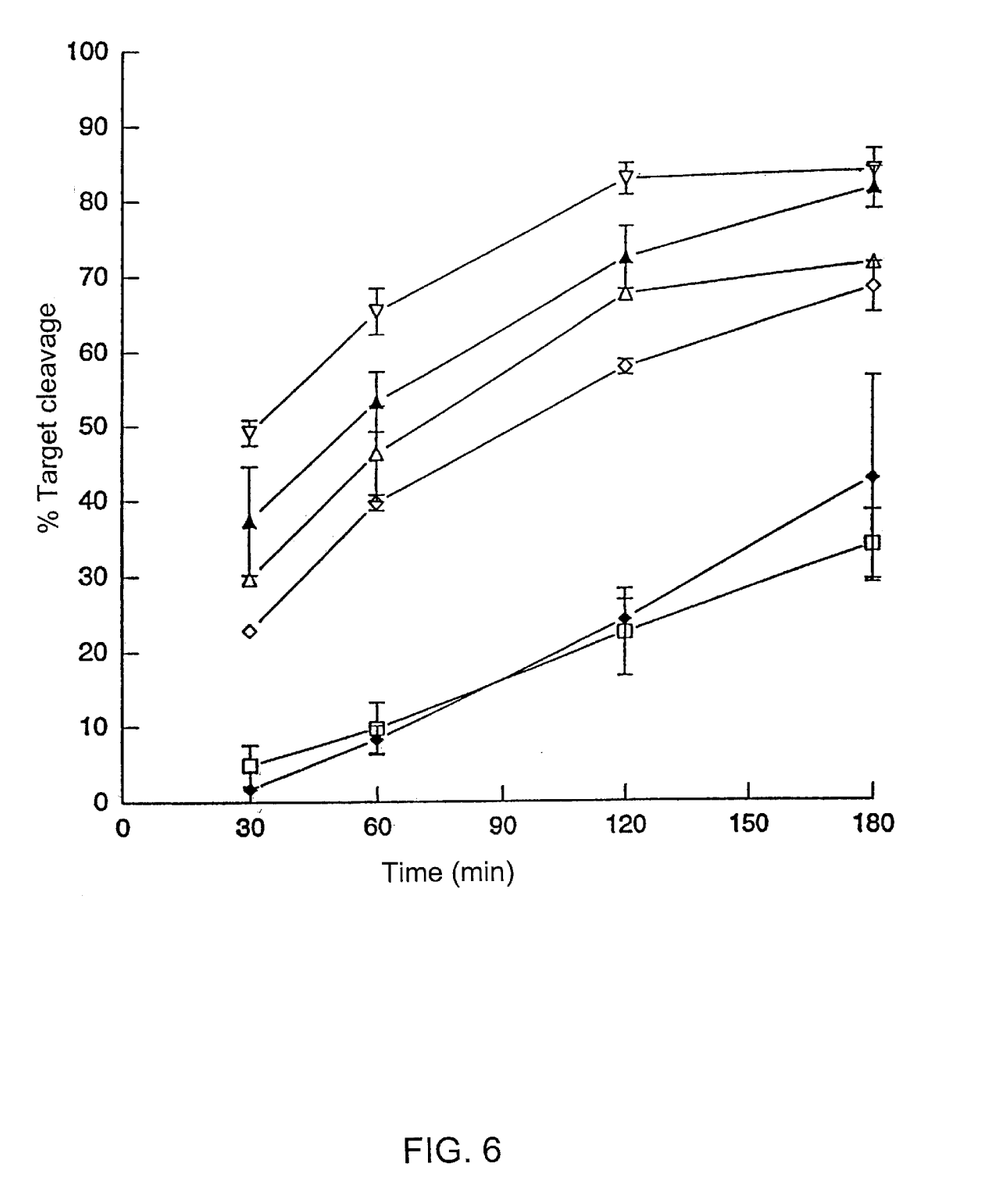
FIG. 6 is a graphic representation of the time course of cleavage (%) of the target RNA transcript by the pentameric ribozyme at various ratios of ribozyme to target with and without preincubation. The pentameric ribozyme at ratios of 0.2:1, 2:1 and 10:1 without preincubation is indicated by an open square, open diamond and closed triangle, respectively. The pentameric ribozyme at ratios of 0.2:1, 2:1 and 10:1 with preincubation is indicated by a closed diamond, open triangle and inverted open triangle, respectively.

Furthermore, the incubation of equimolar amounts of pentameric ribozymes and target produced the same efficiency of cleavage as a ten-fold molar excess of the short single ribozyme, and was significantly more active than a ten molar excess of the long monomeric transcript. This is particularly important in light of the fact that, because of the time needed for the release of a significant proportion of the monomeric units from the multimeric transcripts, the number of active molecules was in fact much smaller. Corroborating this observation, the addition of a preincubation step of the ribozyme before the addition of the target was translated into an overall increase in the cleavage rates (FIG. 6). These results may be due to the reduction of non-productive folding and hybridization of the ribozyme due to the removal of extra flanking sequences. The resulting monomers are in fact similar in size to the chemically synthesized ribozymes and have the additional advantage that they do not need repeated administration to achieve a lasting effect.

Thus, this invention has several applications. The multimeric self-cleavable ribozymes of the present invention have utility for RNA-targeted gene therapy in both plants and animals to down-regulate endogenous gene expression by cleaving mRNA transcripts produced by a gene of interest. For instance, the multimeric self-cleaving ribozyme of the present invention can be used to target and cleave viral RNA in order to inhibit the replication cycle of viruses such as HIV, hepatitis B virus (HBV), bovine leukemia virus (BLV) and human T-cell leukemia viruses (HTLV-I and -II).

The multimeric self-cleavable ribozyme of the present invention can also be used to inhibit expression of genes belonging to other infectious agents, including viruses, bacteria and protozoa, or genes whose products have deleterious effects on an organism in particular situations (i.e., inflammation in autoimmune diseases, vascular restenosis after angioplasty, defective metabolic enzymes such as the alpha-l-antitrypsin). The present invention also has application to genes involved in the control of cell growth and differentiation. These genes include those of cell cycle regulators (cyclins, cyclin dependent kinases), growth factors, growth factor receptors and second messengers, and the present invention has particular utility for the inhibition of oncogenes.

A vector comprising DNA encoding the multimeric ribozyme of the present invention can be delivered to an appropriate location in a living organism, e.g., particular organs or cell types, and the DNA incorporated in the vector can be expressed. Upon expression, the multimeric ribozyme is cleaved into its individual monomeric units, and at least one of the monomeric units recognizes and cleaves a transcript including the target recognition sequence comprising the ribozyme cleavage site transcribed from the gene of interest or a portion thereof. Thus, the transcript is cleaved and expression of the gene is down-regulated or inhibited.

The ribozyme of the present invention can also be used in virtually any application in which highly efficient, sequence-specific cleavage and destruction of RNA transcripts is desired.

These multimeric self-cleavable molecules also have practical application as RNA molecular weight markers or in preparing an RNA molecular weight ladder. Incomplete self cleavage produces a family of RNA pieces, all of which are multiples of the monomeric unit. Thus, multiple fragments of predictable size can be generated and used as standards to determine molecular weights of unknown RNAs. Present technology utilizes different standards for the synthesis of the bands in commercially available RNA molecular weight markers. The present system requires only one template, considerably reducing the amount of necessary time and work.

The following examples are offered for the purpose of illustrating the present invention and are not to be construed to limit the scope of the present invention:

EXAMPLES

Construction of Ribozymes and Expression Vectors

Cloning procedures resulted in the generation of three self-cleavable constructs containing one, five and ten copies of the anti-HBV ribozyme (pBMRz, pB5T-MRz and pB10T-MRz, respectively) and one plasmid containing one unit of the ribozyme without the self-cleaving motif (pBRz). Plasmid constructs were checked by restriction enzyme patterns, and correct sequence and direction of the pentameric plasmid was assessed by sequencing.

Figure 1B:
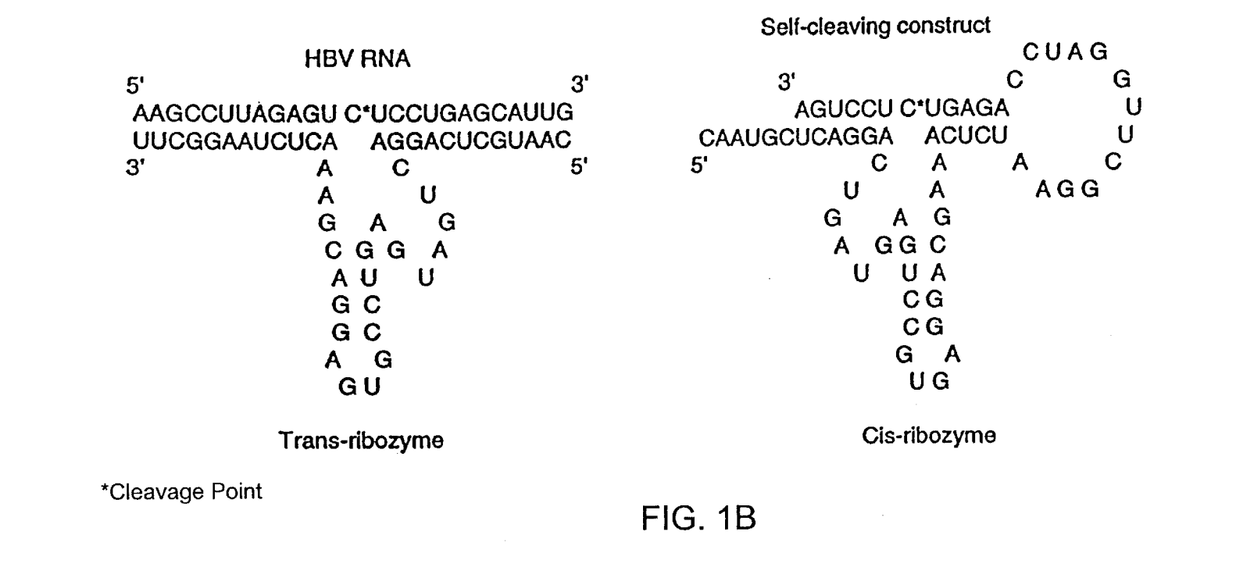

Two 78 nucleotide oligonucleotides encoding a ribozyme against the core region of the hepatitis B virus, nucleotides 2021–2045, and the elements necessary for further subcloning (FIG. 1) were synthesized, annealed and cloned into a XbaI-HindIII site in Bluescript™ SK+, to create pBMRz. In order to make the molecule self-cleavable, the target motif recognized by the ribozyme was introduced downstream from the catalytic sequence.

Figure 7:
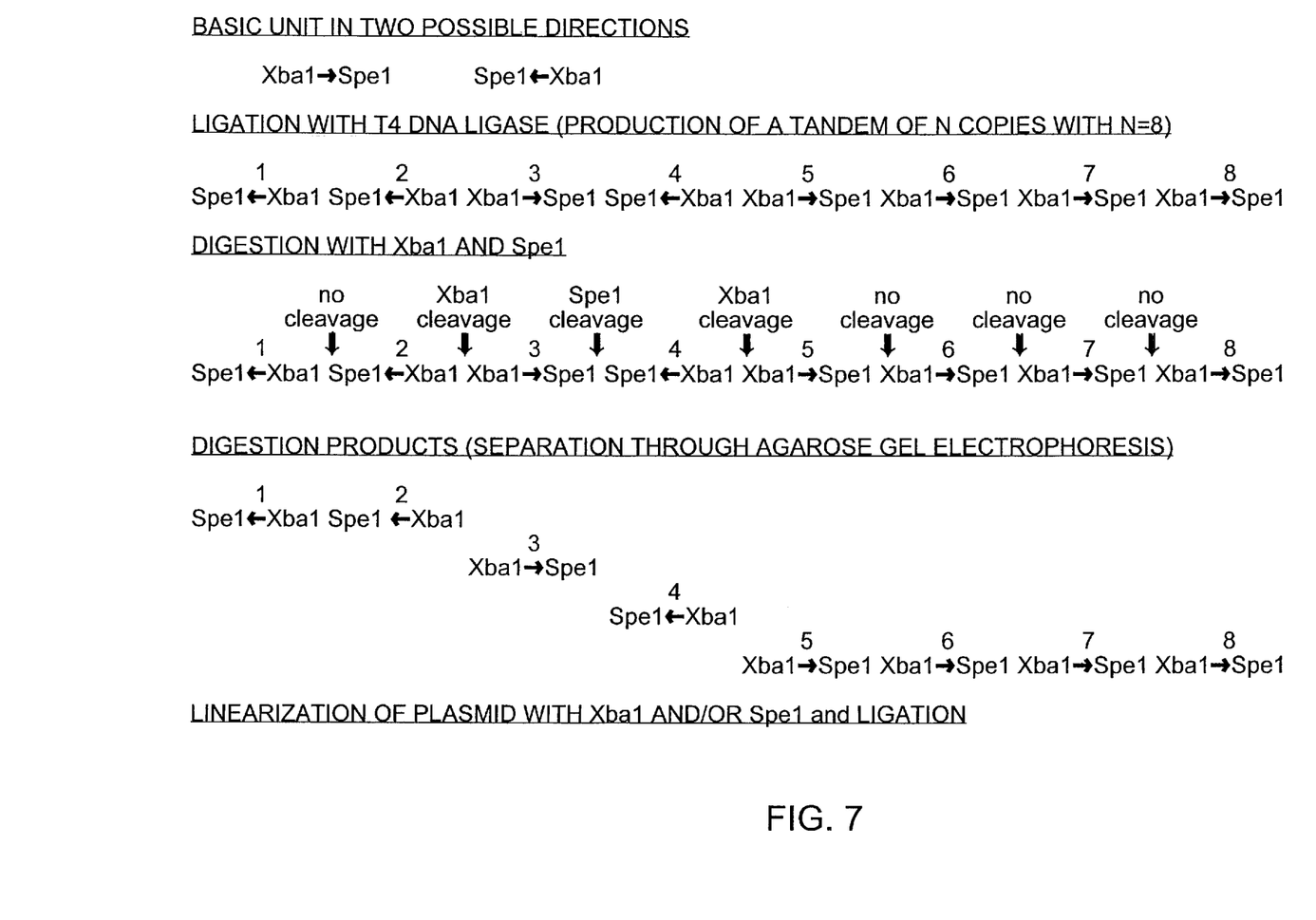
FIG. 7 is an illustration of the cloning strategy for constructing the multimeric ribozymes of the present invention utilizing restriction enzymes which are isoschizomers.

The strategy used to prepare the repeats of self-cleavable ribozymes was based on the use of restriction enzymes that are isoschizomers; that is, utilizing restriction enzymes which have the same recognition site, although they do not necessarily cleave at the same position (FIG. 7). The recognition sites for XbaI and SpeI were introduced into the basic cloning unit at each end of the molecule (FIG. 1A). Fragments produced by digestion with one of these enzymes can be cloned into fragments produced by the other; however, after ligation those restriction sites are lost and are no longer recognized by either enzyme. If a second digestion with both enzymes is performed, ends that the ligase has joined with the same restriction enzyme termini (XbaI/XbaI or SpeI/SpeI) will be cut, but not those that contain an XbaI end joined to a SpeI site, and vice versa. The combination of successive ligation and digestion reactions can increase the length of the product and assure the directionality of the final product.

According to this scheme, pBMRz was digested with XbaI-SpeI, and the 70 nucleotide fragment containing the ribozyme was separated by agarose gel electrophoresis, recovered from the gel and allowed to self-ligate with T4 DNA ligase (Gibco-BRL). A second digestion with XbaI- SpeI was performed and the products separated in a 16 agarose gel. A band containing four copies of the ribozyme was purified and ligated into XbaI-linearized pBMRz to create pB5T-MRz. Correct nucleotide composition and direction of the ribozyme was confirmed by sequencing reaction. Following the same procedure a second plasmid (pB10T-MRz) containing 10 copies of the ribozyme was created.

An expression vector containing a single copy of the ribozyme without the self-cleaving motif (pBRz) was cloned by ligating an XbaI/BamHI pBMRz fragment into Bluescript™ SK+.

In vitro Expression of Ribozymes and HBV RNA Target

Figure 2A:
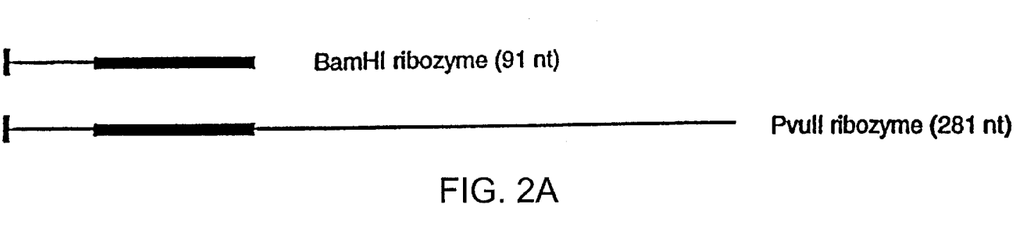
FIGS. 2A and 2B illustrate a schematic of the ribozyme constructs.
Figure 2B:
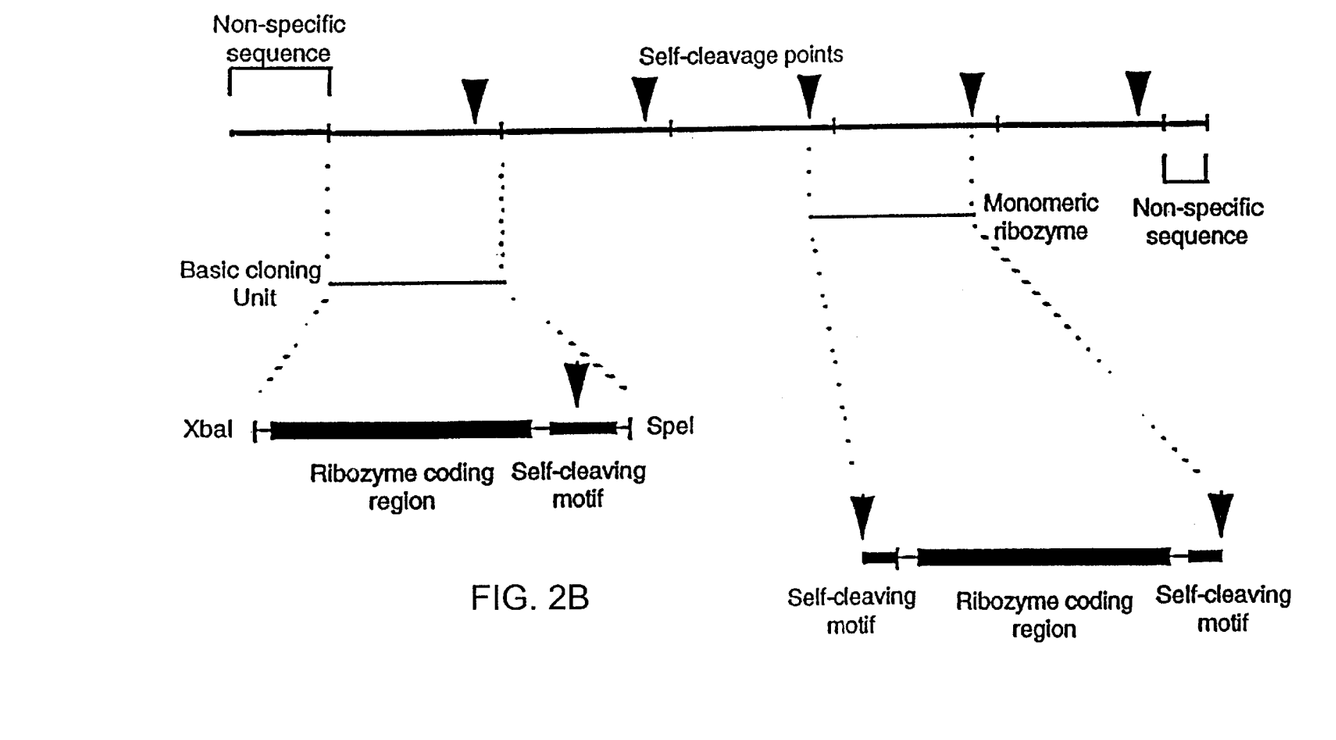

Transcription reactions from linearized plasmids were carried out as previously described by Milligan and Uhlenbeck (*Methods in Enzymol.* 180:51–62 (1989)). pBMRz was linearized with KpnI to assess the self-cleaving properties of the molecule; pB5T-MRz and pB10T-MRz were digested with HindIII to assay the kinetics of self-cleavage of the multimeric ribozyme and trans-cleavage activity; finally, pBRz was linearized with BamHI and PvuII to produce monomeric ribozymes truncated, or extended, at the 3' end of the ribozyme motif, respectively. FIG. 2 shows the structure of the pentameric (FIG. 2B), the truncated, and the long monomeric ribozymes (FIG. 2A).

The HBV RNA substrate used for trans-ribozyme cleavage reactions was transcribed from a 1.2 kilobase SspI fragment purified from ADWR9, a plasmid containing 2 head-to-tail copies of the hepatitis B viral genome (obtained from Dr. T. Jake Liang, Massachusetts General Hospital, Boston, Mass.). The 858 nucleotide-long, T7 RNA polymerase synthesized RNA includes nucleotides 1413–2256 of the HBV genome in the core gene of the pregenomic RNA.

Both cold and $^{32}$P-labelled UTP were used to reduce the presence of incomplete transcripts during the T3 and T7 RNA polymerase reactions. Also, the nucleotide concentration in the transcription reaction mixture was increased to 8 mM in order to keep the free Mg++ concentration to a minimum and diminish the self-cleavage activity during the transcription reaction.

Cis Self-Cleavage Reaction of Multimeric Ribozyme

Figure 3:
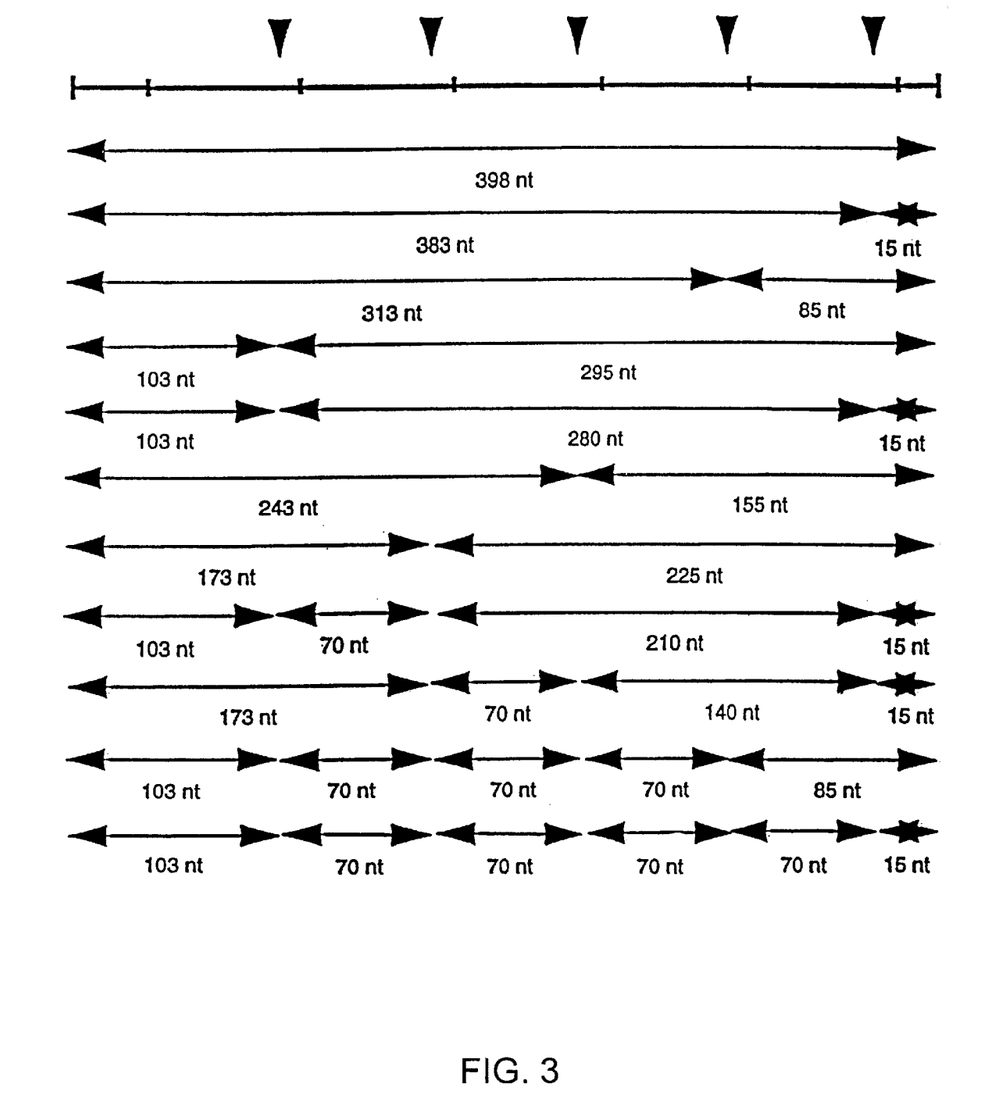
FIG. 3 is a schematic representation of the fragments originating from the self-cleavage of the pentameric ribozyme (pB5T-MRz). This explains the presence of three bands for each different ribozyme unit number (monomers, dimers, etc.) as well as the size of the bands present in the pentameric transcript.

To assess the ability of the different constructs to self-cleave, RNAs were synthesized from each linearized plasmid under standard conditions and the products were resolved in a polyacrylamide denaturing gel (results not shown). The results showed that, without the need for a cleavage incubation step, RNA transcripts processed themselves to produce the expected cleavage bands. The incubation step was not necessary due to the presence of MgCl$_2$ in the transcription buffer. The presence of three bands for each different band present in the pentameric transcript is explained schematically in FIG. 3.

Tubes containing 2 pmoles of the pentameric ribozyme transcript in 18 μl 50 mM Tris-HCl, pH 7.5, were heated to 95° C. for 3 minutes and cooled on ice. The cleavage reaction was started by the addition of 2 μl of 100 mM MgCl$_2$. Samples were incubated at 37° C. for 3 hours and aliquots were taken at different times. Reactions were immediately stopped by the addition of 100 mM EDTA. The influence of the presence of the target RNA on the self-cleavage reaction was assessed under the same conditions described above, except that 2 pmoles of cold HBV RNA were added. Labelled pentameric ribozyme (2 pmoles) was loaded after synthesis, or after 3 hours incubation at 37° C. in the absence of MgCl$_2$, and after different incubation periods at 37° C. with MgCl$_2$ alone or in the presence of an equimolar amount of cold target RNA (results not shown).

The efficiency of cleavage for monomeric units at time 0 (released during transcription) was calculated to be 17.7%. After 3 hours incubation, the efficiency of cleavage reached nearly 80%. The presence of the HBV RNA target did not influence the self-cleavage reaction at any point in time (FIG. 4).

In vitro Trans Cleavage Ribozyme Reaction

Both target and ribozyme transcripts were mixed at different ratios, and reactions were carried out under the conditions described above. The effect of the number of released monomeric ribozyme molecules from the pentameric transcript on the trans-cleavage reaction was assessed by including a pre-incubation step (37° C. for 3 hours) prior to the addition of the target HBV RNA.

In order to compare the activity of monomeric non-self-cleaving ribozymes with multimeric transcripts, two pBRz-derived RNAs varying in the length of the sequence downstream from the catalytic motif were synthesized. BamHI or PvuII were used to generate a shorter (91 nucleotides) or longer (281 nucleotides) monomeric ribozyme respectively (FIG. 2A). The difference between these two transcripts was the presence of 190 extra nucleotides derived from Bluescript at the 3' end of the PvuII synthesized RNA. In addition, both RNAs contained the same 44 nucleotide derived from Bluescript upstream from the ribozyme motif. The multimeric ribozyme consisted of a 398 nucleotide RNA synthesized from a HindIII digestion of pB5T-MRz containing 5 units of the ribozyme.

To assess the extent of self-cleavage of pentameric ribozymes during the reaction and correlate it with overall trans-cleavage results, some reactions included (besides labelled target RNA) $^{32}$P-labelled multimeric transcripts. Self-cleavage of this molecule releases monomeric units with 12 nucleotide, non-specific flanking regions at both sides.

Cleavage products were resolved in denaturing 5% polyacrylamide-8 M urea gels, and results were quantitatively analyzed with a PhosphoroImager (Molecular Dynamics). Cleavage percentages were calculated as a P1+P2/S+P1+P2 where P1 and P2 are the cleavage products and S is the full length HBV RNA. All experiments were performed at least in duplicate, and most were done in triplicate.

A comparison of the trans-cleavage activities of a short BamHI monomeric transcript and the pentameric ribozyme was made using 2 pmoles HBV RNA after synthesis (no ribozyme or incubation), 2 pmoles HBV RNA and 2 pmoles monomeric ribozyme (1:1 ratio), 2 pmoles HBV RNA and 20 pmoles monomeric ribozyme (1:10 ratio), 2 pmoles HBV RNA and 0.4 pmoles pentameric ribozyme (1:0.2 ratio), 2 pmoles HBV RNA and 2 pmoles pentameric ribozyme (1:1 ratio), and 2 pmoles HBV RNA and 20 pmoles pentameric ribozyme (1:10 ratio). Cleavage products appearing as bands of the expected size were clearly visible. As expected, the highest cleavage rate (79%) was obtained with a ten-fold molar excess of the pentameric ribozyme over target RNA, incubated for 3 hours. Interestingly, cleavage results were similar at every time point (18.3% vs. 15.3%, 26.8% vs. 24.8%, 45.6% vs. 48.9% and 55.4% vs. 58.3%), although samples incubated in a ten-fold molar excess of the BamHI monomeric ribozyme would have at best half the number of molecules of the non-processing monomeric ribozyme.

Figure 5:
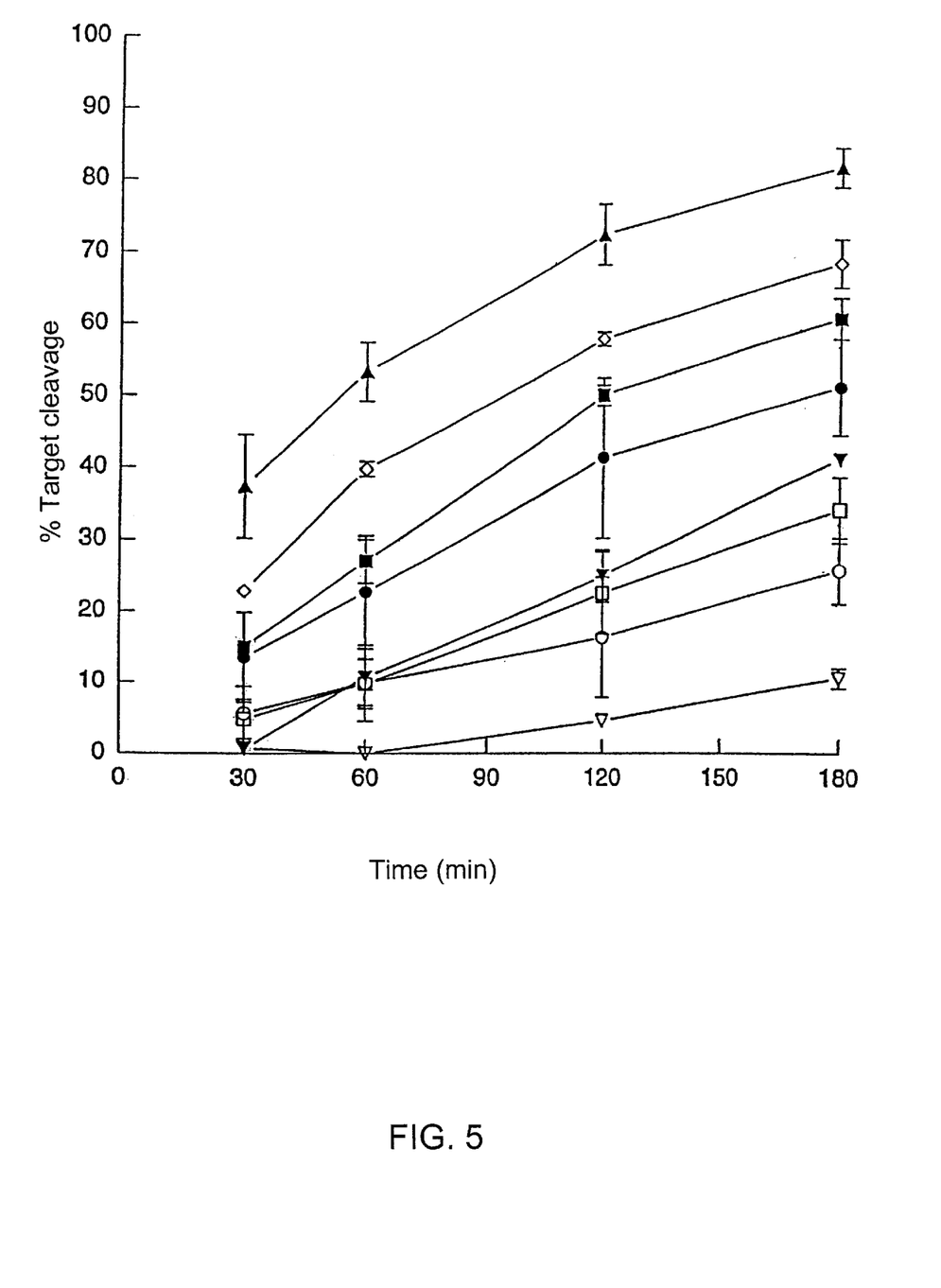
FIG. 5 is a graphic representation of the time course of target transcript cleavage (%) of various constructs and ratios of ribozyme to target. The BamHI ribozyme at a ratio of 1:1 is indicated with an open circle. The BamHI ribozyme at a 10:1 ratio is indicated with a closed circle. The PvuII ribozyme at a ratio of 1:1 is indicated with an open inverted triangle. The PvuII ribozyme at a ratio of 10:1 is indicated with a closed inverted triangle. The pentameric ribozyme at a ratio of 0.2:1 is indicated with an open square. The pentameric ribozyme at a ratio of 1:1 is indicated with a closed square. The pentameric ribozyme at a ratio of 2:1 is indicated with an open diamond. The pentameric ribozyme at a ratio of 10:1 is indicated with a closed triangle.

FIG. 5 summarizes the cleavage results obtained under the different conditions tested. Molar ratios used for pentameric ribozymes (0.2:1, 1:1, 2:1 and 10:1 ribozyme to target) were designed to match the number of non-self-processed ribozymes (used in 1:1 and 10:1 ratio) either as RNA transcripts (1:1 and 10:1) or as ribozyme units 0.2:1 and 2:1). It can be seen that even considering a smaller number of ribozyme units (ratios 1:1 for pentameric ribozymes vs. 10:1 for monomeric ribozymes), pentameric transcripts are as effective as short non-self-cleavable molecules (BamHI generated) and significantly better than long single ribozyme transcripts (PvuII generated). Furthermore, when the same number of ribozyme units are compared between groups (ratios of 0.2:1 and 2:1 for pentameric ribozymes vs. 1:1 and 10:1 for monomeric ribozymes), multimeric transcripts are not only more effective than long single ribozymes (PvuII), but also than its shorter counterparts (BamHI) after three hours of incubation. Finally, for the same number of transcripts (1:1 and 10:1 for both pentameric and monomeric transcripts), significant differences in the efficiency of cleavage of the target were found at every time point during the experiments, independent of the length of the non-cleavable ribozyme molecule considered.

Effect of Pre-incubation on Trans-Activity of Multimeric Ribozymes

Previous results of the comparison of trans cleavage activities of single vs. multimeric ribozymes were based on theoretical calculations of the number of ribozyme units that could be released from the pentameric transcripts after a fully completed self-cleavage reaction. However, the self-cleavage kinetics demonstrated progressive liberation of monomeric units that reached nearly 80% after 3 hours incubation (FIG. 4). This means that the actual number of active ribozyme monomers involved in the trans-cleavage reaction with shorter incubation times in the previous experiments was in fact lower than the maximum theoretically generated. To study the effect of an increased number of monomers at early incubation times on the overall HBV RNA cleavage, experiments were repeated using the same ribozyme to target ratios, but pentameric ribozymes were pre-incubated for three hours before the target was added. Results of these experiments are shown in FIG. 6. As expected, activities were greatly increased, specifically during the first two hours of the trans-cleavage reaction. By the end of the incubation, cleavage values approached those obtained with non pre-incubated multimeric ribozymes.

Equivalents

Those skilled in the art will recognize, or be able to ascertain using no more than routine experimentation, many equivalents to the specific embodiments of the invention described herein. Such equivalents are intended to be encompassed by the following claims:

We claim:

1. A multimeric self-cleaving ribozyme construct, comprising multiple operably linked self-cleaving monomeric units, wherein each unit comprises:
   a) a ribozyme which functions both in cis and in trans comprising a catalytic domain and an antisense domain; and
   b) a target recognition sequence containing a ribozyme cleavage site recognizable by said antisense domain, wherein said target recognition sequence is the same as the target recognition sequence of a target transcript or a portion of the target transcript sequence which retains the ribozyme cleavage site and is recognized by said antisense domain.

2. The multimeric self-cleaving ribozyme construct of claim 1, wherein the ribozyme of (a) is a hammerhead ribozyme.

3. The multimeric self-cleaving ribozyme construct of claim 1, wherein the target recognition sequence is derived from the core region of the pregenomic hepatitis B virus RNA transcript.

4. The multimeric self-cleaving ribozyme construct of claim 3, wherein the target recognition sequence is SEQ ID NO.: 1 or a portion thereof containing the ribozyme cleavage site.

5. A method of cleaving an RNA transcript comprising a target recognition sequence, comprising the steps of:
   a) obtaining a vector having incorporated therein DNA encoding a multimeric self-cleaving ribozyme construct according to claim 1 wherein the antisense domain recognizes the RNA transcript;
   b) causing the vector of step (a) to express the DNA encoding the multimeric self-cleaving ribozyme construct, whereby upon expression the multimeric ribozyme is cleaved into its individual monomeric units; and
   c) combining the product of step (b) with the RNA transcript, whereby at least one of the monomeric units recognizes and cleaves the RNA transcript.

6. The method according to claim 5, wherein step (b) and step (c) occur simultaneously.

7. DNA encoding the multimeric self-cleaving ribozyme construct of claim 1.

8. A vector having incorporated therein DNA encoding the multimeric self-cleaving ribozyme construct of claim 1.

9. A composition comprising the vector of claim 8 and a physiologically acceptable vehicle.

10. A cell comprising the vector of claim 8.

11. A method of regulating the expression of a gene or a portion thereof, comprising the steps of:

a) introducing into a cell a vector having incorporated therein DNA encoding a multimeric self-cleaving ribozyme construct according to claim 1, wherein the antisense domain recognizes an RNA transcript containing the target recognition sequence comprising a ribozyme cleavage site transcribed from the gene or a portion thereof, whereby a transformed cell is obtained; and b) maintaining the transformed cell to cause expression of the DNA incorporated in the vector, whereby upon expression the multimeric self-cleaving ribozyme construct is cleaved into its individual monomeric units, and whereby at least one of the individual monomeric units recognizes and cleaves the RNA transcript transcribed from the gene or a portion thereof, thereby regulating the expression of the gene or a portion thereof.

12. A method of regulating the expression of a gene or a portion thereof in a living organism, comprising the steps of:

a) delivering a vector to an appropriate location in a living organism, said vector having incorporated therein DNA encoding a multimeric self-cleaving ribozyme construct according to claim 1, wherein the antisense domain recognizes an RNA transcript containing the target recognition sequence comprising a ribozyme cleavage site transcribed from the gene or a portion thereof, b) causing the vector of step (a) to express the DNA encoding the multimeric self-cleaving ribozyme construct, whereby upon expression the multimeric ribozyme is cleaved into its individual monomeric units, and whereby at least one of the individual monomeric units recognizes and cleaves the RNA transcript transcribed from the gene or a portion thereof, thereby regulating the expression of the gene or a portion thereof in a living organism.

13. A method of preparing an RNA molecular weight ladder, comprising the steps of:

a) obtaining a multimeric self-cleaving ribozyme construct according to claim 1; and b) treating the multimeric ribozyme construct of step (a) such that incomplete self-cleavage occurs, thereby generating an RNA molecular weight ladder comprising RNA molecular weight markers of predictable size and weight.

14. An RNA molecular weight marker produced by the method of claim 13.

* * * * *

```
                              SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:1:

AAGCCUUAGA GUCUCCUGAG CAUUG                                              25

(2) INFORMATION FOR SEQ ID NO:2:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

CAAUGCUCAG GACUGAUGAG UCCGUGAGGA CGAAACUCUA AGGCUU                       46

(2) INFORMATION FOR SEQ ID NO:3:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:
```

```
CTAGACAATG CTCAGGACTG ATGAGTCCGT GAGGACGAAA CTCTAAGGCT TGGATCCAGA         60

GTCTCCTGAA CTAGTCCA                                                      78

(2) INFORMATION FOR SEQ ID NO:4:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

TGTTACGAGT CCTGACTACT CAGGCACTCC TGCTTTGAGA TTCCGAACCT AGGTCTCAGA         60

GGACTTGATC AGGTTCGA                                                      78

(2) INFORMATION FOR SEQ ID NO:5:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:5:

GAGUCUCCUG A                                                             11

(2) INFORMATION FOR SEQ ID NO:6:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:6:

CAAUGCUCAG GACUGAUGAG UCCGUGAGGA CGAAACUCUA AGGCUUGGAU CCAGAGUCUC         60

CUGA                                                                     64
```